US012400340B2

(12) United States Patent
Buharin (10) Patent No.: US 12,400,340 B2
(45) Date of Patent: Aug. 26, 2025

(54) USER INTERFACE ELEMENTS FOR ORIENTATION OF REMOTE CAMERA DURING SURGERY

(71) Applicant: Activ Surgical, Inc., Boston, MA (US)

(72) Inventor: Vasiliy Evgenyevich Buharin, Boston, MA (US)

(73) Assignee: ACTIV Surgical, Inc., Boston, MA (US)

(*) Notice: Subject to any disclaimer, the term of this patent is extended or adjusted under 35 U.S.C. 154(b) by 928 days.

(21) Appl. No.: 17/356,353

(22) Filed: Jun. 23, 2021

(65) Prior Publication Data

US 2022/0020160 A1 Jan. 20, 2022

Related U.S. Application Data

(63) Continuation of application No. PCT/US2019/068756, filed on Dec. 27, 2019.
(Continued)

(51) Int. Cl.
*A61B 1/05* (2006.01)
*A61B 1/00* (2006.01)
(Continued)

(52) U.S. Cl.
CPC ............ *G06T 7/248* (2017.01); *A61B 34/20* (2016.02); *A61B 34/25* (2016.02); *A61B 34/30* (2016.02); *A61B 34/70* (2016.02); *A61B 90/37* (2016.02); *G06T 7/277* (2017.01); *G06T 7/292* (2017.01); *G16H 30/20* (2018.01); *G16H 40/63* (2018.01); *G16H 40/67* (2018.01); *A61B 2034/2057* (2016.02); *A61B 2034/2059* (2016.02);
(Continued)

(58) Field of Classification Search
None
See application file for complete search history.

(56) References Cited

U.S. PATENT DOCUMENTS

| 4,772,831 A | 9/1988 | Casler, Jr. et al. |
| 5,808,665 A | 9/1998 | Green |

(Continued)

FOREIGN PATENT DOCUMENTS

| CN | 103425971 A | * 12/2013 | |
| CN | 104271046 A | * 1/2015 | ............. A61B 34/20 |

(Continued)

OTHER PUBLICATIONS

U.S. Appl. No. 17/338,030 Office Action dated Oct. 4, 2023.
(Continued)

*Primary Examiner* — Mohammed Rachedine
(74) *Attorney, Agent, or Firm* — Cesari and McKenna, LLP (57) ABSTRACT

User interface elements for orientation of remote camera during surgery are provided. In various embodiments, an image of an interior of a body cavity of a patient is received from one or more camera located at a distal end of an endoscopic tool. Position information and/or orientation information of the camera is received. A reference view indicating a field of view of the camera(s) on an anatomical model is generated based on the position information and/or orientation information. The reference view is displayed in combination with the image to a user.

19 Claims, 7 Drawing Sheets

Related U.S. Application Data (60) Provisional application No. 62/786,003, filed on Dec. 28, 2018.

(51) Int. Cl.

| | | |
|---|---|---|
| A61B 34/00 | (2016.01) | |
| A61B 34/10 | (2016.01) | |
| A61B 34/20 | (2016.01) | |
| A61B 34/30 | (2016.01) | |
| A61B 90/00 | (2016.01) | |
| G06T 7/246 | (2017.01) | |
| G06T 7/277 | (2017.01) | |
| G06T 7/292 | (2017.01) | |
| G16H 30/20 | (2018.01) | |
| G16H 40/63 | (2018.01) | |
| G16H 40/67 | (2018.01) | |

(52) U.S. Cl.
CPC ... *A61B 2034/302* (2016.02); *A61B 2090/371* (2016.02); *A61B 2090/374* (2016.02); *A61B 2090/3762* (2016.02); *A61B 2090/378* (2016.02); *A61B 2562/0219* (2013.01); *G06T 2207/30004* (2013.01); *G06T 2207/30244* (2013.01)

(56) References Cited

U.S. PATENT DOCUMENTS

| | | |
|---|---|---|
| 5,876,325 A | 3/1999 | Mizuno et al. |
| 6,001,108 A | 12/1999 | Wang et al. |
| 6,088,105 A | 7/2000 | Link |
| 6,183,485 B1 | 2/2001 | Thomason et al. |
| 6,206,894 B1 | 3/2001 | Thompson et al. |
| 6,223,100 B1 | 4/2001 | Green |
| 6,309,397 B1 | 10/2001 | Julian et al. |
| 6,325,808 B1 | 12/2001 | Bernard et al. |
| 6,373,963 B1 | 4/2002 | Demers et al. |
| 6,491,702 B2 | 12/2002 | Heilbrun et al. |
| 6,503,195 B1 | 1/2003 | Keller et al. |
| 6,542,249 B1 | 4/2003 | Kofman et al. |
| 6,549,288 B1 | 4/2003 | Migdal et al. |
| 6,563,105 B2 | 5/2003 | Seibel et al. |
| 6,564,086 B2 | 5/2003 | Marchitto et al. |
| 6,613,041 B1 | 9/2003 | Schrunder |
| 6,643,563 B2 | 11/2003 | Hosek et al. |
| 6,645,196 B1 | 11/2003 | Nixon et al. |
| 6,697,164 B1 | 2/2004 | Babayoff et al. |
| 6,800,057 B2 | 10/2004 | Tsujita et al. |
| 6,850,872 B1 | 2/2005 | Marschner et al. |
| 6,873,867 B2 | 3/2005 | Vilsmeier |
| 6,885,464 B1 | 4/2005 | Pfeiffer et al. |
| RE38,800 E | 9/2005 | Barbour |
| 6,965,690 B2 | 11/2005 | Matsumoto |
| 6,977,732 B2 | 12/2005 | Chen et al. |
| 6,987,531 B2 | 1/2006 | Kamon |
| 7,006,236 B2 | 2/2006 | Tomasi et al. |
| 7,068,825 B2 | 6/2006 | Rubbert et al. |
| 7,092,107 B2 | 8/2006 | Babayoff et al. |
| 7,099,732 B2 | 8/2006 | Geng |
| 7,124,066 B2 | 10/2006 | Marschner et al. |
| 7,152,024 B2 | 12/2006 | Marschner et al. |
| 7,184,150 B2 | 2/2007 | Quadling et al. |
| 7,200,262 B2 | 4/2007 | Sawada |
| 7,224,384 B1 | 5/2007 | Iddan et al. |
| 7,230,725 B2 | 6/2007 | Babayoff et al. |
| 7,242,997 B2 | 7/2007 | Geng |
| 7,305,110 B2 | 12/2007 | Rubbert et al. |
| 7,313,264 B2 | 12/2007 | Crampton |
| 7,319,529 B2 | 1/2008 | Babayoff |
| 7,363,201 B2 | 4/2008 | Marschner et al. |
| 7,385,708 B2 | 6/2008 | Ackerman et al. |
| 7,433,807 B2 | 10/2008 | Marschner et al. |
| 7,435,217 B2 | 10/2008 | Wiklof |
| 7,450,783 B2 | 11/2008 | Talapov et al. |
| 7,477,402 B2 | 1/2009 | Babayoff et al. |
| 7,489,408 B2 | 2/2009 | Harding et al. |
| 7,491,956 B2 | 2/2009 | Knoche et al. |
| 7,492,927 B2 | 2/2009 | Marschner et al. |
| 7,511,829 B2 | 3/2009 | Babayoff |
| 7,522,764 B2 | 4/2009 | Schwotzer |
| 7,577,299 B2 | 8/2009 | Kawamata et al. |
| 7,620,209 B2 | 11/2009 | Stevick et al. |
| 7,630,089 B2 | 12/2009 | Babayoff et al. |
| 7,704,206 B2 | 4/2010 | Suzuki et al. |
| 7,724,378 B2 | 5/2010 | Babayoff |
| 7,724,932 B2 | 5/2010 | Ernst et al. |
| 7,751,871 B2 | 7/2010 | Rubbert |
| 7,763,841 B1 | 7/2010 | McEldowney |
| 7,794,388 B2 | 9/2010 | Draxinger et al. |
| 7,821,649 B2 | 10/2010 | Bendall et al. |
| 7,854,700 B2 | 12/2010 | Orihara |
| 7,898,651 B2 | 3/2011 | Hu et al. |
| 7,944,569 B2 | 5/2011 | Babayoff et al. |
| 7,951,073 B2 | 5/2011 | Freed |
| 7,959,557 B2 | 6/2011 | Weitzner et al. |
| 7,961,912 B2 | 6/2011 | Stevick et al. |
| 7,967,743 B2 | 6/2011 | Ishihara |
| 7,990,548 B2 | 8/2011 | Babayoff et al. |
| 7,995,798 B2 | 8/2011 | Krupnik et al. |
| 8,027,710 B1 | 9/2011 | Dannan |
| 8,038,609 B2 | 10/2011 | Kohno et al. |
| 8,052,636 B2 | 11/2011 | Moll et al. |
| 8,084,753 B2 | 12/2011 | Joshi et al. |
| 8,257,303 B2 | 9/2012 | Moll et al. |
| 8,264,536 B2 | 9/2012 | McEldowney |
| 8,279,418 B2 | 10/2012 | Yee et al. |
| 8,280,152 B2 | 10/2012 | Thiel et al. |
| 8,310,683 B2 | 11/2012 | Babayoff et al. |
| 8,320,621 B2 | 11/2012 | McEldowney |
| 8,326,020 B2 | 12/2012 | Lee et al. |
| 8,330,804 B2 | 12/2012 | Lutian et al. |
| 8,395,342 B2 | 3/2013 | Prisco |
| 8,400,494 B2 | 3/2013 | Zalevsky et al. |
| 8,406,859 B2 | 3/2013 | Zuzak et al. |
| 8,471,897 B2 | 6/2013 | Rodriguez Ramos et al. |
| 8,517,928 B2 | 8/2013 | Orihara |
| 8,553,939 B2 | 10/2013 | Craig et al. |
| 8,558,873 B2 | 10/2013 | McEldowney |
| 8,593,507 B2 | 11/2013 | Yahav |
| 8,610,665 B2 | 12/2013 | Craig et al. |
| 8,617,102 B2 | 12/2013 | Moll et al. |
| 8,649,024 B2 | 2/2014 | Colonna De Lega |
| 8,659,765 B2 | 2/2014 | Ando |
| 8,723,118 B2 | 5/2014 | McEldowney et al. |
| 8,723,923 B2 | 5/2014 | Bloom et al. |
| 8,755,053 B2 | 6/2014 | Fright et al. |
| 8,792,098 B2 | 7/2014 | Dewald et al. |
| 8,803,952 B2 | 8/2014 | Katz et al. |
| 8,823,790 B2 | 9/2014 | Dunn et al. |
| 8,891,087 B2 | 11/2014 | Zuzak et al. |
| 8,896,594 B2 | 11/2014 | Xiong et al. |
| 8,974,378 B2 | 3/2015 | Imaizumi et al. |
| 9,001,190 B2 | 4/2015 | Olivier, III et al. |
| 9,057,784 B2 | 6/2015 | Hudman |
| 9,068,824 B2 | 6/2015 | Findeisen et al. |
| 9,070,194 B2 | 6/2015 | Lee et al. |
| 9,072,445 B2 | 7/2015 | Berguer et al. |
| 9,074,868 B2 | 7/2015 | Bendall et al. |
| 9,089,277 B2 | 7/2015 | Babayoff et al. |
| 9,119,552 B2 | 9/2015 | Baumann et al. |
| 9,135,502 B2 | 9/2015 | Haker et al. |
| 9,142,025 B2 | 9/2015 | Park et al. |
| 9,147,253 B2 | 9/2015 | Yee et al. |
| 9,149,281 B2 | 10/2015 | Bonutti |
| 9,149,348 B2 | 10/2015 | Wu et al. |
| 9,155,544 B2 | 10/2015 | Bonutti |
| 9,157,728 B2 | 10/2015 | Ogawa |
| 9,157,733 B2 | 10/2015 | Dillon et al. |
| 9,186,053 B2 | 11/2015 | Viola |
| 9,192,395 B2 | 11/2015 | Bonutti |
| 9,198,578 B2 | 12/2015 | Zuzak et al. |
| 9,204,952 B2 | 12/2015 | Lampalzer |

(56) References Cited

U.S. PATENT DOCUMENTS

| | | |
|---|---|---|
| 9,220,570 B2 | 12/2015 | Kim et al. |
| 9,226,645 B2 | 1/2016 | Ntziachristos |
| 9,226,673 B2 | 1/2016 | Ferguson, Jr. et al. |
| 9,226,811 B2 | 1/2016 | Abuzaina |
| 9,247,865 B2 | 2/2016 | Igarashi et al. |
| 9,254,076 B2 | 2/2016 | McDowall |
| 9,254,078 B2 | 2/2016 | McDowall |
| 9,254,103 B2 | 2/2016 | Krishnaswamy et al. |
| 9,261,356 B2 | 2/2016 | Lampert et al. |
| 9,261,358 B2 | 2/2016 | Atiya et al. |
| 9,271,658 B2 | 3/2016 | Ferguson, Jr. et al. |
| 9,274,047 B2 | 3/2016 | Velten et al. |
| 9,282,926 B2 | 3/2016 | Schwotzer et al. |
| 9,294,758 B2 | 3/2016 | Xiong et al. |
| 9,297,889 B2 | 3/2016 | Hudman et al. |
| 9,304,603 B2 | 4/2016 | Miller |
| 9,330,464 B1 | 5/2016 | Ackerman et al. |
| 9,345,389 B2 | 5/2016 | Nie et al. |
| 9,345,392 B2 | 5/2016 | Saito |
| 9,345,397 B2 | 5/2016 | Taylor et al. |
| 9,351,643 B2 | 5/2016 | Sharonov |
| 9,364,300 B2 | 6/2016 | Tchouprakov et al. |
| 9,375,844 B2 | 6/2016 | Itkowitz et al. |
| 9,377,295 B2 | 6/2016 | Fright et al. |
| 9,380,224 B2 | 6/2016 | Keskin et al. |
| 9,389,068 B2 | 7/2016 | Ri |
| 9,402,986 B2 | 8/2016 | Bell et al. |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,457,168 B2 | 10/2016 | Moll et al. |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,557,574 B2 | 1/2017 | McEldowney |
| 9,581,802 B2 | 2/2017 | Yokota |
| 9,585,600 B2 | 3/2017 | Sharonov |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,662,018 B2 | 5/2017 | Stopek |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,821,456 B2 | 11/2017 | Riedel |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,943,964 B2 | 4/2018 | Hares |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,130,345 B2 * | 11/2018 | Wong .................... A61B 34/37 |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,154,378 B2 * | 10/2021 | Tesar ................. A61B 1/00193 |
| 11,197,722 B2 * | 12/2021 | Tako ..................... G16H 20/40 |
| 11,278,220 B2 | 3/2022 | Tucker et al. |
| 2003/0083650 A1 | 5/2003 | Wang et al. |
| 2003/0083651 A1 | 5/2003 | Wang et al. |
| 2003/0195623 A1 | 10/2003 | Marchitto et al. |
| 2004/0073257 A1 | 4/2004 | Spitz |
| 2004/0176751 A1 | 9/2004 | Weitzner et al. |
| 2005/0090840 A1 | 4/2005 | Gerbino et al. |
| 2005/0096515 A1 | 5/2005 | Geng |
| 2006/0020272 A1 | 1/2006 | Gildenberg |
| 2006/0258938 A1 | 11/2006 | Hoffman et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0213749 A1 | 9/2007 | Kogasaka et al. |
| 2007/0232855 A1 | 10/2007 | Weitzner et al. |
| 2007/0239178 A1 | 10/2007 | Weitzner et al. |
| 2007/0249911 A1 | 10/2007 | Simon |
| 2007/0250072 A1 | 10/2007 | Weitzner et al. |
| 2007/0250097 A1 | 10/2007 | Weitzner et al. |
| 2007/0280423 A1 | 12/2007 | Schmidt |
| 2007/0293734 A1 | 12/2007 | Coste-Maniere et al. |
| 2008/0013809 A1 | 1/2008 | Zhu et al. |
| 2008/0107305 A1 | 5/2008 | Vanderkooy et al. |
| 2008/0177281 A1 | 7/2008 | Weitzner et al. |
| 2008/0266391 A1 | 10/2008 | Lee et al. |
| 2009/0221874 A1 | 9/2009 | Vinther et al. |
| 2009/0244260 A1 | 10/2009 | Takahashi et al. |
| 2009/0326324 A1 | 12/2009 | Munoz Martinez et al. |
| 2010/0081875 A1 | 4/2010 | Fowler et al. |
| 2010/0113921 A1 | 5/2010 | Fear et al. |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0080471 A1 | 4/2011 | Song et al. |
| 2011/0123098 A1 | 5/2011 | Ernst et al. |
| 2011/0202068 A1 | 8/2011 | Diolaiti et al. |
| 2012/0075432 A1 | 3/2012 | Bilbrey et al. |
| 2012/0095354 A1 | 4/2012 | Dunn et al. |
| 2012/0130405 A1 | 5/2012 | Cohn et al. |
| 2012/0165681 A1 | 6/2012 | Keller |
| 2012/0206587 A1 | 8/2012 | Oz et al. |
| 2012/0310098 A1 | 12/2012 | Popovic |
| 2013/0023732 A1 | 1/2013 | Kim et al. |
| 2013/0079928 A1 | 3/2013 | Søe-Knudsen et al. |
| 2013/0085595 A1 | 4/2013 | Kiley et al. |
| 2013/0096576 A1 | 4/2013 | Cooper et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2013/0304084 A1 | 11/2013 | Beira et al. |
| 2013/0331644 A1 | 12/2013 | Pandya et al. |
| 2014/0031665 A1 | 1/2014 | Pinto et al. |

(56) References Cited

U.S. PATENT DOCUMENTS

| | | |
|---|---|---|
| 2014/0052005 A1 | 2/2014 | Yokota |
| 2014/0071257 A1 | 3/2014 | Yokota |
| 2014/0092281 A1 | 4/2014 | Nisenzon et al. |
| 2014/0148816 A1 | 5/2014 | McDonald et al. |
| 2014/0148819 A1 | 5/2014 | Inoue et al. |
| 2014/0194747 A1 | 7/2014 | Kruglick et al. |
| 2014/0243850 A1 | 8/2014 | Sadaka |
| 2014/0257329 A1 | 9/2014 | Jang et al. |
| 2014/0277741 A1 | 9/2014 | Kwon et al. |
| 2015/0012016 A1 | 1/2015 | Stone |
| 2015/0164329 A1 | 6/2015 | Schmidt et al. |
| 2015/0238276 A1 | 8/2015 | Atarot et al. |
| 2015/0266183 A1 | 9/2015 | Alifragkis et al. |
| 2015/0319424 A1* | 11/2015 | Haimovitch-Yogev ............ H04N 23/661 348/48 |
| 2015/0377613 A1 | 12/2015 | Small et al. |
| 2016/0128553 A1 | 5/2016 | Geng |
| 2016/0136805 A1 | 5/2016 | Soe-Knudsen et al. |
| 2016/0139039 A1 | 5/2016 | Ikehara et al. |
| 2016/0157942 A1 | 6/2016 | Gombert et al. |
| 2016/0206391 A1 | 7/2016 | Deodhar |
| 2016/0239978 A1 | 8/2016 | Cole et al. |
| 2016/0260206 A1 | 9/2016 | Jung et al. |
| 2016/0262615 A1 | 9/2016 | Jung et al. |
| 2016/0278678 A1 | 9/2016 | Valdes et al. |
| 2016/0296225 A1 | 10/2016 | Rohl et al. |
| 2016/0300348 A1 | 10/2016 | Nadeau et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2016/0346930 A1 | 12/2016 | Hares |
| 2017/0014030 A1 | 1/2017 | Rentschler et al. |
| 2017/0020393 A1 | 1/2017 | Rentschler et al. |
| 2017/0020615 A1 | 1/2017 | Koenig et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0079724 A1 | 3/2017 | Yang et al. |
| 2017/0100024 A1 | 4/2017 | Shahmoon et al. |
| 2017/0112368 A1* | 4/2017 | Stern ............... A61B 34/37 |
| 2017/0143237 A1 | 5/2017 | Yokota |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0209031 A1 | 7/2017 | Nakamura et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0280970 A1 | 10/2017 | Sartor et al. |
| 2017/0328704 A1 | 11/2017 | Atiya et al. |
| 2017/0333030 A1 | 11/2017 | Bourland, III et al. |
| 2017/0347043 A1 | 11/2017 | Rephaeli et al. |
| 2017/0347868 A1 | 12/2017 | Zoellner et al. |
| 2017/0366773 A1 | 12/2017 | Kiraly et al. |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0165823 A1 | 6/2018 | Ludwig |
| 2018/0174318 A1 | 6/2018 | Wang et al. |
| 2018/0214241 A1 | 8/2018 | Furuta et al. |
| 2018/0235715 A1 | 8/2018 | Amiot et al. |
| 2018/0243043 A1 | 8/2018 | Michihata et al. |
| 2018/0329504 A1* | 11/2018 | Ziraknejad ............ G06F 3/017 |
| 2018/0338806 A1* | 11/2018 | Grubbs ............... A61B 34/30 |
| 2018/0345492 A1 | 12/2018 | Watanabe et al. |
| 2019/0038362 A1* | 2/2019 | Nash ................ A61B 90/36 |
| 2020/0305721 A1 | 10/2020 | Chen et al. |
| 2021/0030277 A1 | 2/2021 | Ferguson, Jr. et al. |
| 2021/0282654 A1 | 9/2021 | Cha et al. |
| 2021/0354285 A1 | 11/2021 | Buharin et al. |
| 2022/0000557 A1 | 1/2022 | Dehghani |
| 2022/0015844 A1 | 1/2022 | Dehghani |
| 2022/0175471 A1 | 6/2022 | Pickett et al. |

FOREIGN PATENT DOCUMENTS

| | | | |
|---|---|---|---|
| CN | 105596005 | 5/2016 | |
| CN | 109480791 A * | 3/2019 | |
| EP | 2672715 A2 | 12/2013 | |
| WO | WO-2004004320 A1 * | 1/2004 | ......... G06K 9/00234 |
| WO | WO-2010096447 A2 | 8/2010 | |
| WO | WO-2010096453 A1 | 8/2010 | |
| WO | WO-2012096878 A2 | 7/2012 | |
| WO | WO-2014152753 A1 | 9/2014 | |
| WO | WO-2015070010 A1 | 5/2015 | |
| WO | WO-2016061052 A1 | 4/2016 | |
| WO | WO-2016153741 A1 | 9/2016 | |
| WO | WO-2017075602 A1 | 5/2017 | |
| WO | WO-2018067515 A1 | 4/2018 | |
| WO | WO-2019045971 A1 | 3/2019 | |
| WO | WO-2020006454 A1 | 1/2020 | |
| WO | WO-2020118244 A1 | 6/2020 | |
| WO | WO-2020140042 | 7/2020 | |
| WO | WO-2020140048 A1 | 7/2020 | |
| WO | WO-2020140056 | 7/2020 | |
| WO | WO-2020214821 | 11/2020 | |
| WO | WO-2022029308 A1 | 2/2022 | |
| WO | WO-2022058499 A1 | 3/2022 | |

OTHER PUBLICATIONS

PCT/US19/068756 Search Report & Written Opinion dated Apr. 1, 2020.

Dunn, et al. Laser speckle contrast imaging in biomedical optics. Journal of Biomedical Optics 15(1), 011109 (Jan./Feb. 2010).

EP19901561.1 Extended European Search Report dated Jan. 4, 2023.

EP19902562.8 Extended Search Report dated Aug. 22, 2022.

Holstein-Rathlou et al. Nephron blood flow dynamics measured by laser speckle contrast imaging. Am J Physiol Renal Physiol 300: F319-F329, 2011.

PCT/US19/068765 Search Report & Written Opinion dated Apr. 1, 2020.

PCT/US19/068778 Search Report & Written Opinion dated Apr. 1, 2020.

PCT/US19/65056 International Search Report and Written Opinion dated Nov. 6, 2020.

PCT/US20/28536 Search Report & Written Opinion dated Jul. 21, 2020.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

* cited by examiner

USER INTERFACE ELEMENTS FOR ORIENTATION OF REMOTE CAMERA DURING SURGERY

CROSS-REFERENCE TO RELATED APPLICATION

This application is a continuation of International Application No. PCT/US2019/068756, filed on Dec. 27, 2019, which application claims the benefit of U.S. Provisional Patent Application No. 62/786,003, filed on Dec. 28, 2018, which applications are incorporated herein by reference in their entirety for all purposes.

BACKGROUND

Embodiments of the present disclosure relate to robotic and endoscopic surgery, and more specifically, to user interface elements for orientation of remote camera during surgery.

BRIEF SUMMARY

According to embodiments of the present disclosure, methods of and computer program products for orienting a camera during a surgical procedure are provided. In various embodiments, a method is performed where an image of an interior of a body cavity of a patient is received from one or more camera. Position information of the one or more camera is received. A reference view indicating a field of view of the one or more camera on an anatomical model is generated based on the position information. The reference view is displayed in combination with the image to a user.

In various embodiments, orientation information of the camera may be received and, based on the orientation information, a direction indicator indicating the direction of the camera may be generated on an anatomical model. In various embodiments, the direction indicator may be displayed in combination with the reference view to the user. In various embodiments, the directional indicator includes an arrow. In various embodiments, the camera includes an absolute position sensor configured to transmit the position information. In various embodiments, the absolute position sensor includes one or more encoder. In various embodiments, the absolute position sensor includes an optical tracking system. In various embodiments, the camera includes an absolute orientation sensor configured to transmit the orientation information. In various embodiments, the absolute orientation sensor includes one or more encoder. In various embodiments, the absolute orientation sensor includes an optical tracking system. In various embodiments, the anatomical model includes a universal atlas. In various embodiments, the anatomical model includes a simplified pictorial representation.

In various embodiments, the anatomical model includes imaging of the patient. In various embodiments, the imaging is received from a picture archiving and communication system (PACS). In various embodiments, the imaging includes at least one of computed tomography (CT), magnetic resonance imaging (MRI), X-ray, ultrasound, and digital imaging. In various embodiments, the imaging of the patient is updated in real time during a medical procedure. In various embodiments, the reference view of the patient is updated in real time during the medical procedure. In various embodiments, the method further includes registering a coordinate space of the camera to a coordinate space of the patient, registering the coordinate space of the camera to a coordinate space of the anatomical model; and receiving depth information of the camera. In various embodiments, positional information of the camera is determined via visual odometry. In various embodiments, displaying of the reference view includes superimposing the reference view on the image. In various embodiments, displaying of the reference view includes displaying the reference view on a supplemental display while displaying the image on a primary display. In various embodiments, the reference view includes a frame indicating a subregion of the reference view where the subregion corresponding to the field of view.

In various embodiments, a system is provided including a digital camera configured to image an interior of a body cavity of a patient, a display, and a computing node including a computer readable storage medium having program instructions embodied therewith. The program instructions are executable by a processor of the computing node to cause the processor to perform a method where an image of an interior of a body cavity of a patient is received from one or more camera. Position information of the one or more camera is received. A reference view indicating a field of view of the one or more camera on an anatomical model is generated based on the position information. The reference view is displayed in combination with the image to a user.

In various embodiments, orientation information of the camera may be received and, based on the orientation information, a direction indicator indicating the direction of the camera may be generated on an anatomical model. In various embodiments, the direction indicator may be displayed in combination with the reference view to the user. In various embodiments, the directional indicator includes an arrow. In various embodiments, the camera includes an absolute position sensor configured to transmit the position information. In various embodiments, the absolute position sensor includes one or more encoder. In various embodiments, the absolute position sensor includes an optical tracking system. In various embodiments, the camera includes an absolute orientation sensor configured to transmit the orientation information. In various embodiments, the absolute orientation sensor includes one or more encoder. In various embodiments, the absolute orientation sensor includes an optical tracking system. In various embodiments, the anatomical model includes a universal atlas. In various embodiments, the anatomical model includes a simplified pictorial representation.

In various embodiments, the anatomical model includes imaging of the patient. In various embodiments, the imaging is received from a picture archiving and communication system (PACS). In various embodiments, the imaging includes at least one of computed tomography (CT), magnetic resonance imaging (MRI), X-ray, ultrasound, and digital imaging. In various embodiments, the imaging of the patient is updated in real time during a medical procedure. In various embodiments, the reference view of the patient is updated in real time during the medical procedure. In various embodiments, the method further includes registering a coordinate space of the camera to a coordinate space of the patient, registering the coordinate space of the camera to a coordinate space of the anatomical model; and receiving depth information of the camera. In various embodiments, positional information of the camera is determined via visual odometry. In various embodiments, displaying of the reference view includes superimposing the reference view on the image. In various embodiments, displaying of the reference view includes displaying the reference view on a supplemental display while displaying the image on a primary display. In various embodiments, the reference view includes a frame indicating a subregion of the reference view where the subregion corresponding to the field of view.

In various embodiments, a computer program product is provided for orienting a camera during a surgical procedure. The computer program product includes a computer readable storage medium having program instructions embodied therewith. The program instructions are executable by a processor to cause the processor to perform a method where an image of an interior of a body cavity of a patient is received from one or more camera. Position information of the one or more camera is received. A reference view indicating a field of view of the one or more camera on an anatomical model is generated based on the position information. The reference view is displayed in combination with the image to a user.

In various embodiments, orientation information of the camera may be received and, based on the orientation information, a direction indicator indicating the direction of the camera may be generated on an anatomical model. In various embodiments, the direction indicator may be displayed in combination with the reference view to the user. In various embodiments, the directional indicator includes an arrow. In various embodiments, the camera includes an absolute position sensor configured to transmit the position information. In various embodiments, the absolute position sensor includes one or more encoder. In various embodiments, the absolute position sensor includes an optical tracking system. In various embodiments, the camera includes an absolute orientation sensor configured to transmit the orientation information. In various embodiments, the absolute orientation sensor includes one or more encoder. In various embodiments, the absolute orientation sensor includes an optical tracking system. In various embodiments, the anatomical model includes a universal atlas. In various embodiments, the anatomical model includes a simplified pictorial representation.

In various embodiments, the anatomical model includes imaging of the patient. In various embodiments, the imaging is received from a picture archiving and communication system (PACS). In various embodiments, the imaging includes at least one of computed tomography (CT), magnetic resonance imaging (MRI), X-ray, ultrasound, and digital imaging. In various embodiments, the imaging of the patient is updated in real time during a medical procedure. In various embodiments, the reference view of the patient is updated in real time during the medical procedure. In various embodiments, the method further includes registering a coordinate space of the camera to a coordinate space of the patient, registering the coordinate space of the camera to a coordinate space of the anatomical model; and receiving depth information of the camera. In various embodiments, positional information of the camera is determined via visual odometry. In various embodiments, displaying of the reference view includes superimposing the reference view on the image. In various embodiments, displaying of the reference view includes displaying the reference view on a supplemental display while displaying the image on a primary display. In various embodiments, the reference view includes a frame indicating a subregion of the reference view where the subregion corresponding to the field of view.

DETAILED DESCRIPTION

An endoscope is an illuminated optical, typically slender and tubular instrument (a type of borescope) used to look within the body. An endoscope may be used to examine internal organs for diagnostic or surgical purposes. Specialized instruments are named after their target anatomy, e.g., the cystoscope (bladder), nephroscope (kidney), bronchoscope (bronchus), arthroscope (joints), colonoscope (colon), laparoscope (abdomen or pelvis).

Laparoscopic surgery is commonly performed in the abdomen or pelvis using small incisions (usually 0.5-1.5 cm) with the aid of a laparoscope. The advantages of such minimally invasive techniques are well-known, and include reduced pain due to smaller incisions, less hemorrhaging, and shorter recovery time as compared to open surgery.

The image available through a single laparoscope is generally two-dimensional, which imposes certain limits on the range of surgeries possible. In addition, the tools used in laparoscopic surgery generally have a limited range of motion, which can make it difficult to work in constrained spaces.

Robotic surgery is similar to laparoscopic surgery insofar as it also uses small incisions, a camera, and various surgical instruments. However, instead of holding and manipulating the surgical instruments directly, a surgeon uses controls to remotely manipulate a robot having one or more surgical instruments. A console provides the surgeon with high-definition images, which allow for increased accuracy and vision.

In the case of robotically-assisted minimally-invasive surgery, instead of directly moving the instruments, the surgeon either uses a telemanipulator or the surgical tools are computer-controlled. A telemanipulator is a remote manipulator that allows the surgeon to perform the normal movements associated with a given surgery. Robotic arms carry out those movements using end-effectors and manipulators to perform the surgery on the patient. In computer-controlled systems, the surgeon uses a computer to control the robotic arms and its end-effectors.

One advantage of robotic surgery is that the surgeon does not have to directly view the surgical site, and in fact need not be present in the operating room at all. However, when viewing a surgical site through a console, the surgeon is isolated from the geometry of that surgical site. In particular, they may become disoriented with regard to direction and scale due to the limited field of view.

An image console can provide three-dimensional, high definition, and magnified images. Various electronic tools may be applied to further aid surgeons. These include visual magnification (e.g., the use of a large viewing screen that improves visibility) and stabilization (e.g., electromechanical damping of vibrations due to machinery or shaky human hands). Simulator may also be provided, in the form of specialized virtual reality training tools to improve physicians' proficiency in surgery.

However, as the image is further manipulated, the surgeon is further insulated from the geometry of the surgical site and may become disoriented.

To help provide orientation to a surgeon during surgery, various embodiments of the present disclosure provide a navigation inset in a digital display. The navigation inset provides a position of the current view relative to an anatomical model. In addition, some embodiments provide an indication of a reference direction, such as up.

Figure 1:
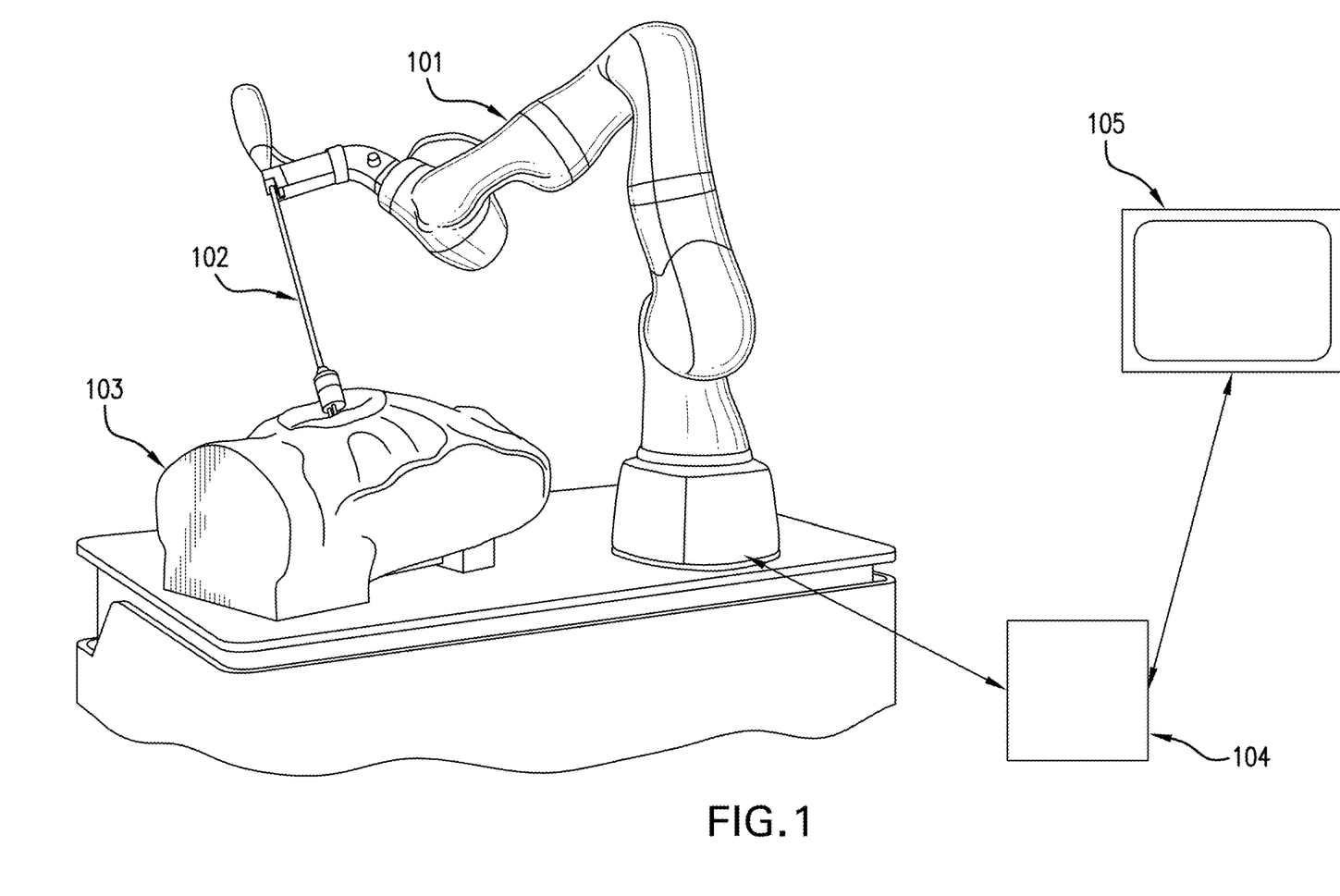
FIG. 1 depicts a system for robotic surgery according to embodiments of the present disclosure.

Referring to FIG. 1, an exemplary robotic surgery setup is illustrated according to the present disclosure. Robotic arm 101 deploys scope 102 within abdomen 103. A digital image is collected via scope 102. In some embodiments, a digital image is captured by one or more digital cameras at the scope tip. In some embodiments, a digital image is captured by one or more fiber optic element running from the scope tip to one or more digital camera elsewhere.

The digital image is provided to computing node 104, where it is processed and then displayed on display 105.

In various embodiments, scope 102 includes one or more position and orientation sensors, for example a magnetometer, gyroscope, and/or range finder. In some embodiments, the position of each joint of arm 101 is tracked, allowing computation of the location and orientation of scope 102 by computing node 104. In some embodiments scope 102 is configured to provide depth data in addition to an image. Based on the sensor output and/or joint positions, computing node 104 determined the location and orientation of the scope relative to the surgical subject. This location may then be correlated to an anatomical model. As set out below, correlation to the anatomical model may be performed based on the depth data, image recognition/atlas registration, and/or registration of the patient to a common coordinate system.

In this way, computing node 104 can generate an indication of the camera position and orientation for display.

Various methods are used to determine which part of the anatomy the camera's field of view is overlaid on. In some embodiments, the patient is registered to the same space that provides the camera coordinates. In such embodiments, the camera location as determined, for example, from the arrangement of each robot joint, is then correlated to the patient in the common coordinate space. In some embodiments, the image captured by the camera is interpreted to identify the anatomy in the field of view. In this way, the field of view may be determined relative to the reference model.

Figure 2:
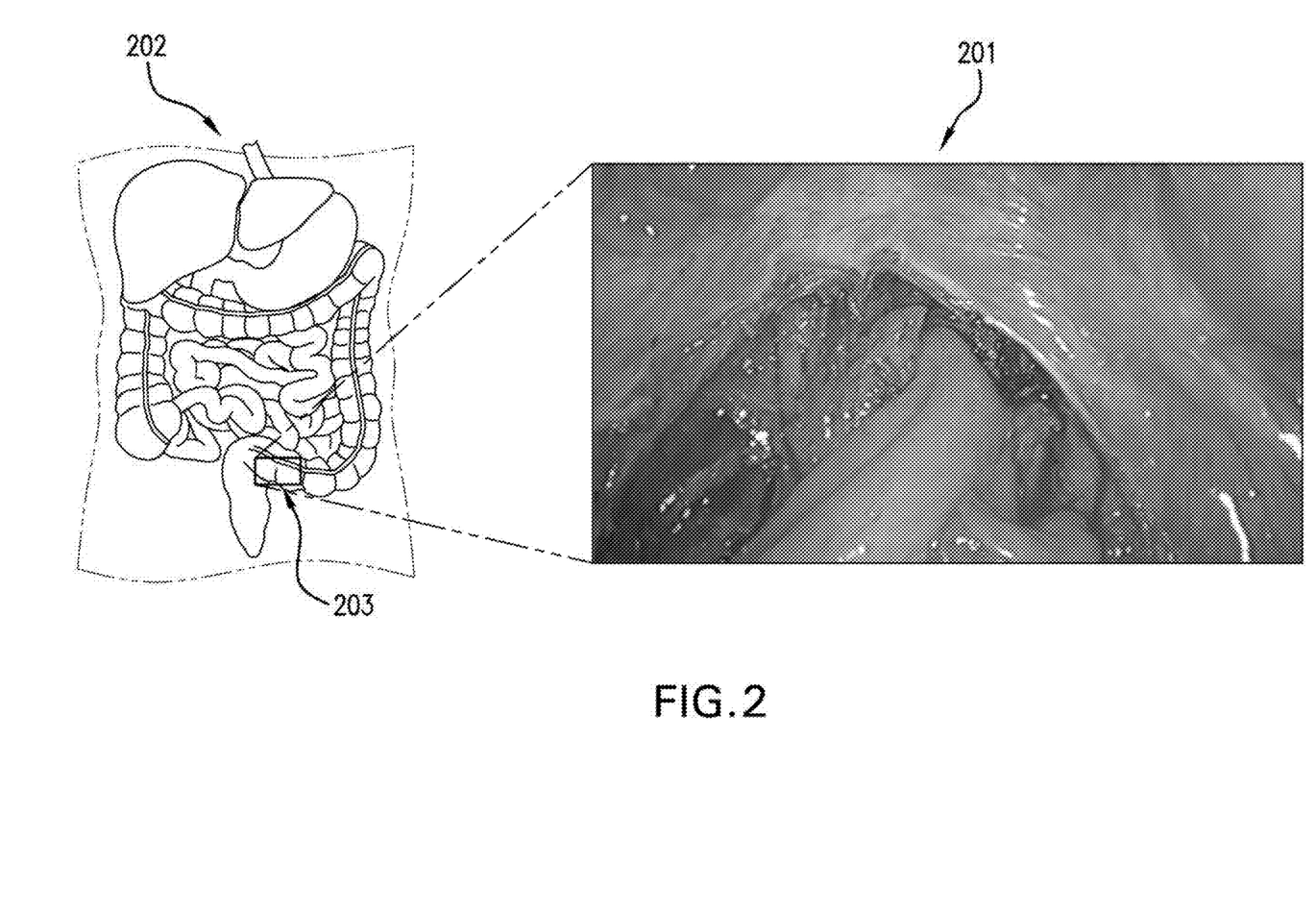
FIG. 2 illustrates an exemplary display according to embodiments of the present disclosure.

Referring to FIG. 2, an exemplary display is provided according to the present disclosure. Image 201 is transmitted from a camera inside the surgical site. In various embodiments, the camera may be provided at the distal end of an endoscopic tool. Based on the location and orientation of the camera, a schematic view 202 is also provided. View 202 includes an anatomical model, for example, of the torso. Frame 203 highlights on the model the extent of image 201. In various embodiments, as the camera moves out and sees a larger portion of the anatomy, this frame resizes to reflect the field of view of the camera.

Figure 3:
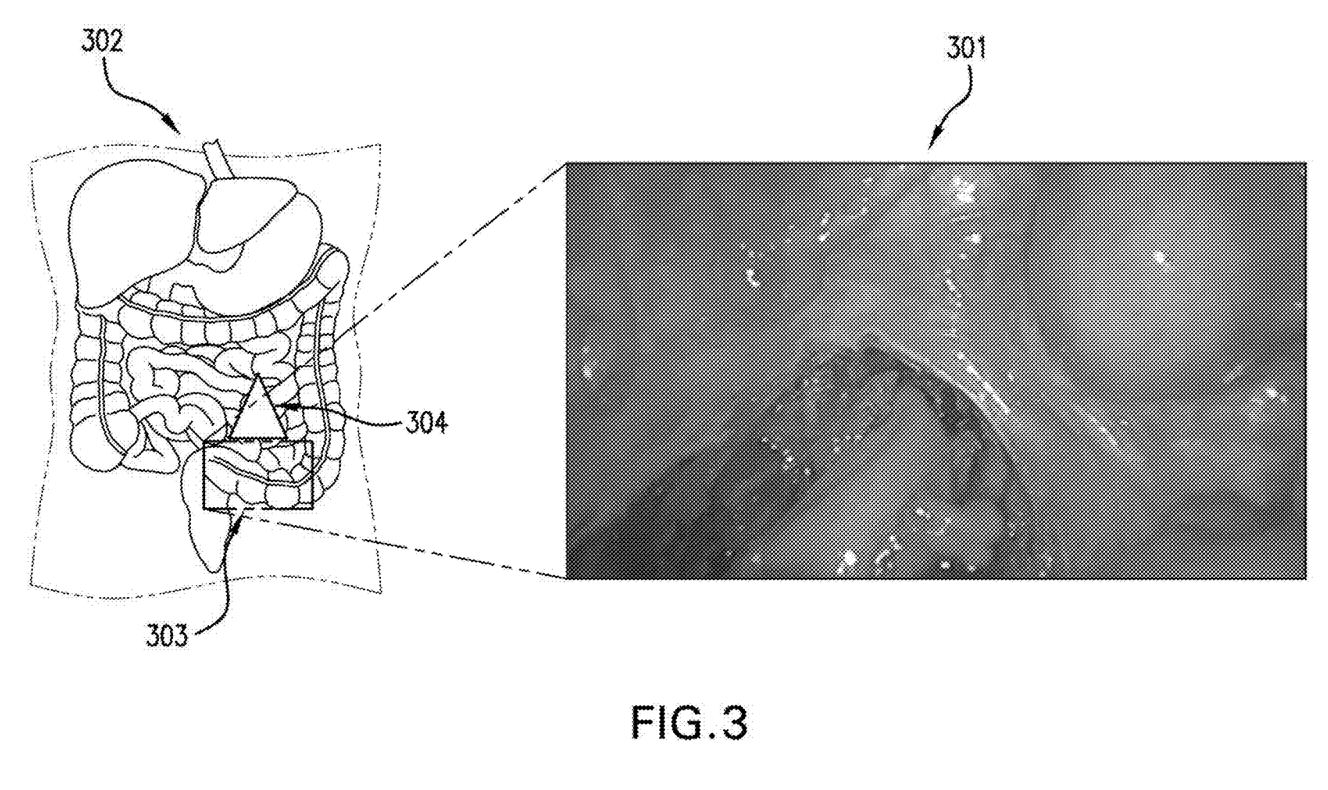
FIG. 3 illustrates a second exemplary display according to embodiments of the present disclosure.

Referring to FIG. 3, a second exemplary display is provided according to the present disclosure. Image 301 is transmitted from a camera inside the surgical site. Based on the location and orientation of the camera, schematic view 302 is also provided. View 302 includes an anatomical model, for example, of the torso. Frame 303 highlights on the model the extent of image 301. In various embodiments, as the camera moves out and sees a larger portion of the anatomy, this frame resizes to reflect the field of view of the camera. Arrow 304 indicated the direction of the camera relative to the anatomical model.

In various embodiments, the surgeon may lock image 301 to maintain a given up direction relative to the patient. In this way, spinning of the camera does not cause the image to spin.

It will be appreciated that the arrangements in FIGS. 2-3 are exemplary, and that other arrangements of the camera view and the reference/schematic view may be used in various embodiments. For example, the reference view may be displayed on a supplemental display separate from the main display containing the camera view. In another example, the reference view is displayed as an inset to the main camera view. In another example, the reference view may be positioned and resized within the main camera view by the surgeon, for example through a touch interface.

Figure 4:
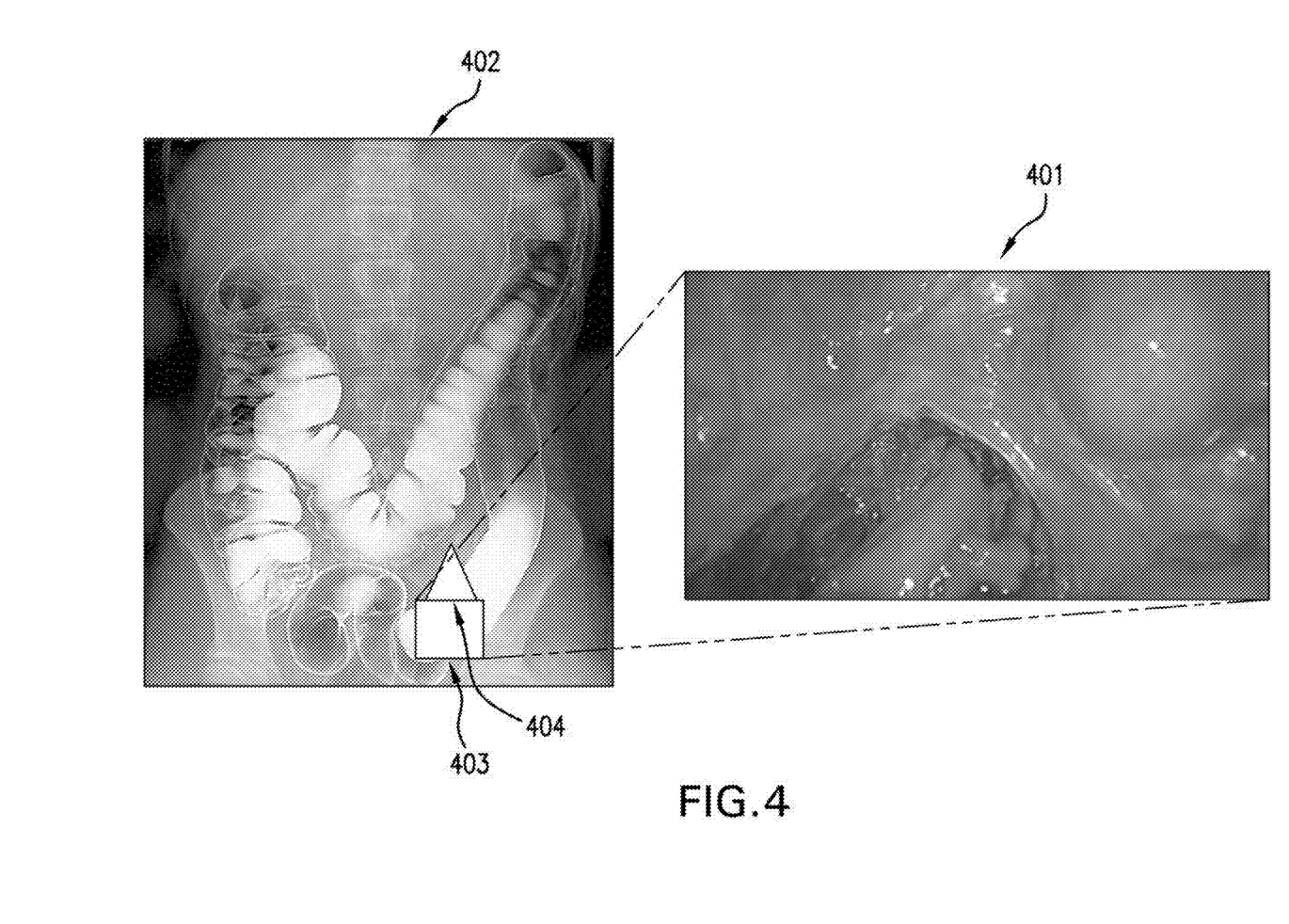
FIG. 4 illustrates a third exemplary display according to embodiments of the present disclosure.

Referring to FIG. 4, a third display is provided according to the present disclosure. Image 401 is transmitted from a camera inside the surgical site (e.g., inside the abdomen of a patient undergoing a laparoscopic procedure). Based on the location and/or orientation of the camera, a schematic view 402 is also provided. View 402 includes an anatomical model, for example, of the torso. Frame 403 highlights on the model the extent of image 401. As the camera moves out and sees a larger portion of the anatomy, this frame resizes to reflect the field of view of the camera. Arrow 404 indicated the direction of the camera relative to the anatomical model.

In various embodiments, the anatomical model may include a universal atlas. In various embodiments, the universal atlas may be a generic representation of human anatomy that seeks to approximate the shapes, positions, and relative locations of the various tissues, organs, bodily structures, etc. In various embodiments, the anatomical model may be a simplified pictorial representation of one or more anatomical objects (e.g., heart, lungs, intestines, bladder, etc.). In various embodiments, the simplified pictorial representation may be a cartoon. In various embodiments, the simplified pictorial representation may include basic shapes to represent the various structures of an anatomical object (e.g., a heart). For example, a heart may be represented as a hollow box or sphere having four cylindrical tubes representing the four major blood vessels (i.e., aorta, vena cava, pulmonary artery, and pulmonary vein).

In various embodiments, the anatomical model may include imaging from the patient. In various embodiments, the imaging may be retrieved from a PACS. In various embodiments, the imaging may include any suitable 2D imaging (e.g., digital imaging, X-ray, CT, MM, ultrasound, etc.) In various embodiments, the imaging may include a 3D reconstruction based on any suitable 2D imaging technique (e.g., a sequence of 2D MRI slices). In various embodiments, the imaging of the patient may be updated in real time during a medical procedure. For example, imaging of the patient may be captured in real time (e.g., using fluoroscopy, intraoperative CT, etc.) and the anatomical model may be updated based on the real-time imaging. For example, if a tissue or organ was shifted by a surgeon out of an original position represented in pre-surgical imaging (e.g., so that the surgeon can access an underlying structure), the real-time imaging would update the position of the shifted tissue or organ in the anatomical model to improve model accuracy.

In various embodiments, the position (e.g., three-dimensional coordinates) and/or orientation (e.g., 3D rotation) of the camera may be determined using absolute position (i.e., location) and absolute orientation. For example, the camera may be mounted on a mechanical arm with one or more encoders to determine absolute position and/or absolute orientation of the camera. In another example, the camera may be tracked with a suitable optical tracking system as is known in the art.

In various embodiments, an absolute position may be determined via RF triangulation (e.g., time delay or phase delay). In various embodiments, the position of the camera may be known even when the operating system is turned off and back on (e.g., during a power outage). In various embodiments, the camera may include a magnetic navigation system. In various embodiments, the camera may include a magnetic sensor. In various embodiments, a magnetic field generator may be placed outside of the surgical site (e.g., under the surgical table).

In various embodiments, the position (e.g., three-dimensional coordinates) and/or orientation (e.g., 3D rotation) of the camera may be determined using relative position (i.e., displacement) and relative orientation. For example, the camera may be fitted with an inertial measurement unit to determine relative position and/or relative orientation of the camera.

In various embodiments, the position of the camera may be determined using one or more of the following sensors: absolute encoders, capacitive displacement sensor, eddy-current sensor, Hall effect sensor, incremental encoder, inductive sensor, laser Doppler, vibrometer (optical), linear encoder, linear variable differential transformer (LVDT), optical encoder, photodiode array, magnetic encoder, piezo-electric transducer (piezo-electric), potentiometer, proximity sensor (optical), rotary encoder (angular), string potentiometer, and/or an ultrasonic sensor.

In various embodiments, an endoscope may include strain sensors to determine, for example, a curvature of the endoscope. In various embodiments, the endoscope may include an optical strain gauge, e.g., Bragg fibers.

In various embodiments, a coordinate space of the camera may be registered with a coordinate space of the patient and/or the anatomical model. In various embodiments, registration of the coordinate space of the camera and the coordinate space of the patient and/or anatomical model may be registered using a calibration matrix. In various embodiments, the calibration matrix may be determined via a least mean squares (LMS) algorithm. In various embodiments, the calibration matrix may be determined via a Kalman filter.

In various embodiments, the coordinate space of the camera may be registered to the coordinate space of the patient and/or model by using anatomical landmarks. In various embodiments, if using an absolute camera position, the camera can be registered to the patient and/or model by pointing the camera at the patient from the outside and identifying landmarks (e.g., bony landmarks such as hip bones and/or sternum). In various embodiments, the same landmarks may be identified in the model. In various embodiments, different landmarks may be identified to align the coordinate spaces of the model and the patient. For example, one (or more) anatomical landmark may be used to align coordinate spaces of camera and patient, while a different (one or more) anatomical landmark may be used to align coordinate spaces of camera and model. In various embodiments, subsequent position of the camera may be reported in absolute units. In various embodiments, the absolute units may be transformed to the patient coordinate space and/or model coordinate space.

In various embodiments, if using relative camera position, the camera can be registered to the patient and/or model by pointing the camera at one or more anatomical landmarks, similar to the absolute position method. In various embodiments, one or more anatomical landmarks are chosen closer to the intended operation site (e.g., liver, esophageal hiatus, kidneys, etc.). In various embodiments, the relative position of the camera may be continuously tracked from the initial registration site. In various embodiments, the relative position of the camera may be transformed to patient and/or model coordinate spaces.

In various embodiments, positional and/or orientation information of the camera may be determined using visual odometry. In various embodiments, one or more image frames (e.g., sequential images) from one or more cameras may be analyzed to determine positional and/or orientation information of the one or more cameras. In various embodiments, visual odometry may be performed in a monocular setup. In various embodiments, visual odometry may be performed in a stereo setup (e.g., two cameras having a known position relative to one another). In various embodiments, the one or more cameras may be calibrated from one or more calibration markers. In various embodiments, the calibration markers may include, for example, one or more known measurements, one or more objects at a known distance, and/or one or more known angular rotations. In various embodiments, the camera may be calibrated to the calibration marker prior to performing a surgical operation (e.g., before insertion into a bodily cavity). In various embodiments, visual odometry may be performed using a feature-based method by extracting image feature points and tracking them in the image sequence. In various embodiments, visual odometry may be performed using a direct method where pixel intensity in the image sequence is used directly as visual input. In various embodiments, visual odometry may be performed using a hybrid method of feature-based and the direct method. In various embodiments, visual odometry may be performed using an inertial measurement unit.

In various embodiments, visual odometry may be performed using the following algorithmic steps. In a first step, input images may be acquired using either single cameras, stereo cameras, or omnidirectional cameras. In a second step, image correction may be performed where image processing techniques are applied for lens distortion removal, etc. In a third step, feature detection may be performed to define interest operators, and match features across frames and construct optical flow field. In feature detection, correlation may be used to establish correspondence of two images, and no long term feature tracking. Feature extraction and correlation may be performed. An optical flow field may be constructed (e.g., Lucas-Kanade method). In a fourth step, flow field vectors are checked for potential tracking errors and to remove outliers. In a fifth step, camera motion is estimated from the optical flow. Estimation of camera motion may be performed through (1) a Kalman filter for state estimate distribution maintenance; or (2) the geometric and 3D properties of the features that minimize a cost function based on the re-projection error between two adjacent images (this can be done by mathematical minimization or random sampling, for example). In a sixth step, periodic repopulation of trackpoints may be performed to maintain coverage across the image. In various embodiments, a direct or appearance-based visual odometry technique may be performed which minimizes an error directly in sensor space and subsequently avoids feature matching and extraction. In various embodiments, another method of visual odometry, known as "visiodometry," may be performed by estimating the planar roto-translations between images using Phase correlation instead of extracting features.

In various embodiments, the one or more cameras may determine position and/or depth from one or more markers in a scene. In various embodiments, the one or more markers may include anatomical landmarks, artificial markers (e.g., dye marker), surgical tool (e.g., suture), etc.

In various embodiments, the one or more cameras may synthesize (e.g., stitch) one or more image frames into a panoramic picture. In various embodiments, the highlighting frame on the anatomical model may be adjusted (e.g., increased in size or decreased in size) based on the panoramic picture generated from the one or more image frames.

Figure 5:
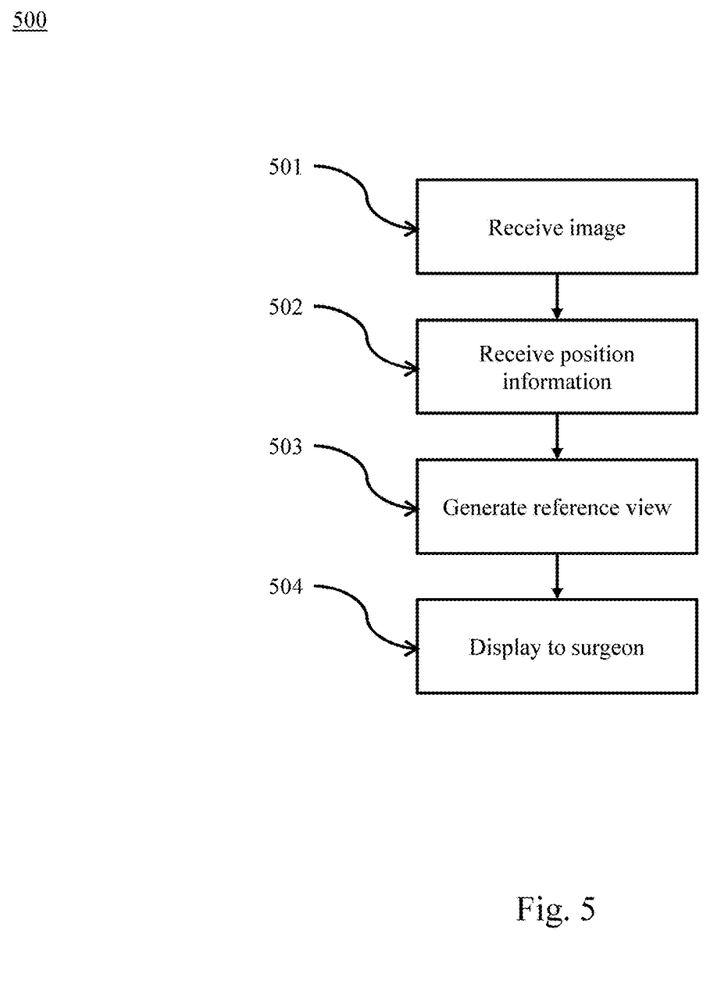
FIG. 5 illustrates a method of orienting an endoscope according to embodiments of the present disclosure.

Referring now to FIG. 5, a method for orienting a camera during a surgical procedure is illustrated according to embodiments of the present disclosure. At 401, an image of an interior of a body cavity is received from a camera. At 402, position information of the camera is received. At 403, a reference view indicating a field of view of the camera on an anatomical model is generated based on the position information. At 404, the reference view is displayed in combination with the image to a user.

Various embodiments of the present disclosure may be adapted for user in gastrointestinal (GI) catheters, such as an endoscope. In particular, the endoscope may include an atomized sprayer, an infrared source, a camera system and optics, one or more robotic arms, and/or an image processor.

In various embodiments, the systems described herein may be configurable at run-time. In various embodiments, one or more patient images (e.g., DICOM images) may be pre-loaded prior to a surgical procedure. In various embodiments, the patient images may be loaded from a PACS. In various embodiments, user preferences may be saved. In various embodiments, user preferences may be loaded upon a particular user logging in to the system.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology reports, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 6:
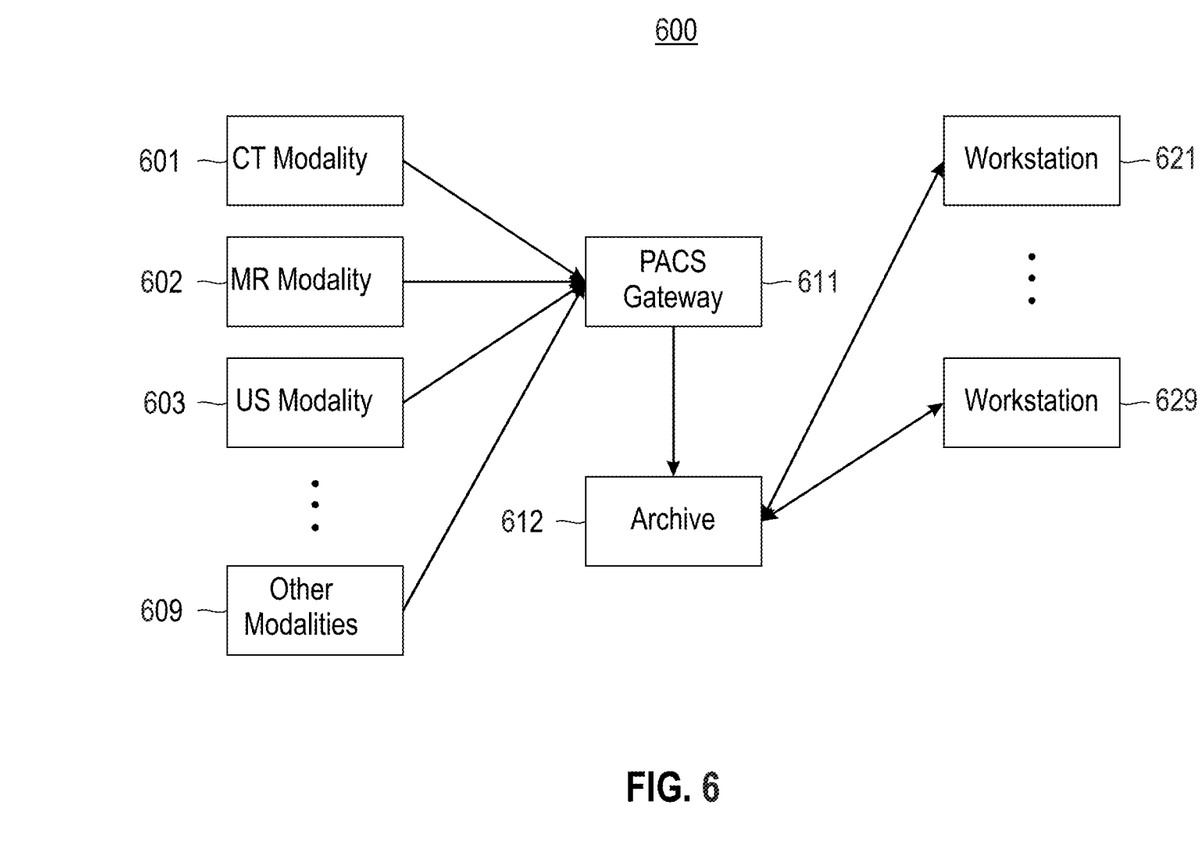
FIG. 6 depicts an exemplary Picture Archiving and Communication System (PACS).

Referring to FIG. 6, an exemplary PACS 600 consists of four major components. Various imaging modalities 601 . . . 609 such as computed tomography (CT) 601, magnetic resonance imaging (MM) 602, or ultrasound (US) 603 provide imagery to the system. In some implementations, imagery is transmitted to a PACS Gateway 611, before being stored in archive 612. Archive 612 provides for the storage and retrieval of images and reports. Workstations 621 . . . 629 provide for interpreting and reviewing images in archive 612. In some embodiments, a secured network is used for the transmission of patient information between the components of the system. In some embodiments, workstations 621 . . . 629 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 611 comprises a quality assurance (QA) workstation. The QA workstation provides a checkpoint to make sure patient demographics are correct as well as other important attributes of a study. If the study information is correct the images are passed to the archive 612 for storage. The central storage device, archive 612, stores images and in some implementations, reports, measurements and other information that resides with the images.

Once images are stored to archive 612, they may be accessed from reading workstations 621 . . . 629. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 621 . . . 629 to burn patient studies for distribution to patients or referring physicians.

In some implementations, a PACS includes web-based interfaces for workstations 621 . . . 629. Such web interfaces may be accessed via the internet or a Wide Area Network (WAN). In some implementations, connection security is provided by a VPN (Virtual Private Network) or SSL (Secure Sockets Layer). The client side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 7:
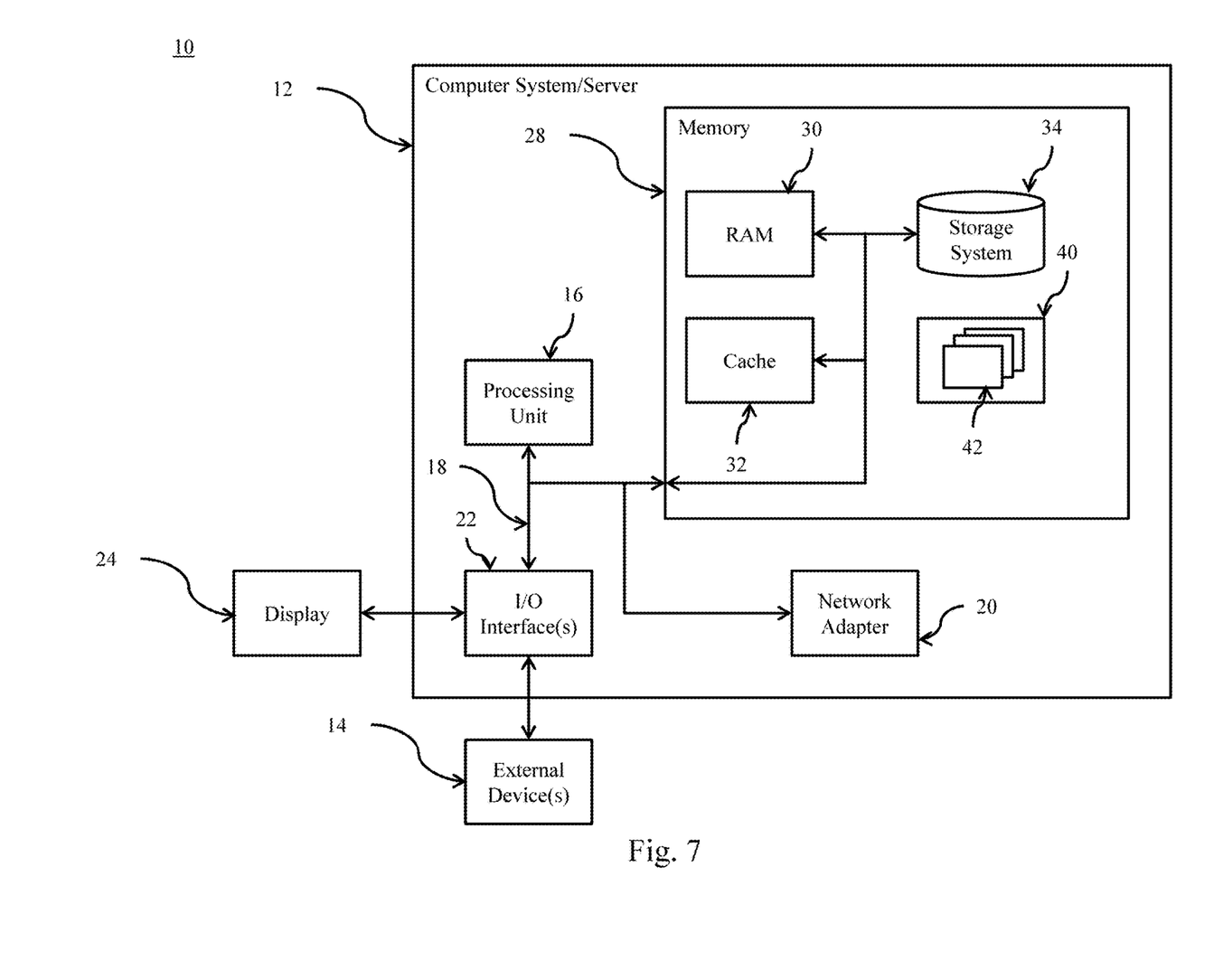
FIG. 7 depicts a computing node according to embodiments of the present disclosure.

Referring now to FIG. 7, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for imaging a surgical scene of a patient, comprising:
    (a) using one or more cameras to capture one or more images of the surgical scene;
    (b) using one or more sensors to obtain position information of the one or more cameras;
    (c) generating a reference view of the surgical scene based on the position information of the one or more cameras, wherein the reference view includes a field of view of the one or more cameras relative to an anatomical model of the surgical scene;
    (d) displaying the reference view and the one or more images of the surgical scene to a user;
    (e) using the one or more sensors to obtain orientation information of the one or more cameras;
    (f) generating a direction indicator based on the orientation information, wherein the direction indicator corresponds to a direction in which the one or more cameras are oriented relative to the anatomical model of the surgical scene; and
    (g) displaying the direction indicator and the reference view to the user.

2. The method of claim 1, wherein the reference view indicates a reference direction to aid in (i) positioning or orienting the one or more cameras or (ii) adjusting the field of view of the one or more cameras relative to one or more regions or features of the surgical scene.

3. The method of claim 1, wherein the direction indicator comprises an arrow.

4. The method of claim 1, wherein the one or more sensors are integrated with the cameras.

5. The method of claim 1, wherein the one or more sensors comprise an absolute position sensor or an absolute orientation sensor.

6. The method of claim 5, wherein the absolute position sensor or the absolute orientation sensor comprises a magnetometer, a gyroscope, a range finder, an encoder, or an optical tracking sensor.

7. The method of claim 1, wherein the anatomical model comprises a universal atlas or a simplified pictorial representation of the surgical scene.

8. The method of claim 1, wherein the anatomical model is generated based on one or more reference images received from a picture archiving and communication system (PACS), which one or more reference images comprise at least one of a computed tomography (CT) image, a magnetic resonance (MRI) image, an X-ray image, an ultrasound image, or a digital image of the patient.

9. The method of claim 8, wherein the one or more reference images are obtained or updated in real time as a medical procedure is being performed in or near the surgical scene.

10. The method of claim 9, wherein the reference view is updated in real time during the medical procedure.

11. The method of claim 1, wherein the position information of the cameras is determined via visual odometry, wherein the visual odometry comprises extracting one or more image feature points from the one or more images and tracking the image feature points in a sequence of images comprising the one or more images.

12. The method of claim 1, wherein displaying the reference view and the one or more images comprises superimposing the reference view on the one or more images, or superimposing the one or more images on the reference view.

13. The method of claim 1, wherein displaying the reference view and the one or more images comprises displaying the reference view on a first display while displaying the one or more images on a second display.

14. A method for imaging a surgical scene of a patient comprising:
    (a) using one or more cameras to (ire one or more images of the surgical scenes;
    (b) using one or more sensors to obtain position in formation of the one or more cameras;
    (c) generating a reference view of the surgical scene based on the position information of the one or more cameras, wherein the reference view includes a field of view of the one or more cameras relative to an anatomical model of the surgical scene;
    (d) registering a coordinate space of the one or more cameras to (i) a coordinate space of the patient and (ii) a coordinate space of the anatomical model;
    (e) obtaining depth information for the surgical scene based at least in part on the registration of the coordinate space of the one or more cameras to the coordinate space of the patient or the coordinate space of the anatomical model;
    (f) displaying the reference view and the one or more images of the surgical scene to a user;
    (g) using the one or more sensors to obtain orientation information of the one or more cameras;
    (h) generating a direction indicator based on the orientation information, wherein the direction indicator corresponds to a direction in which the one or more cameras are oriented relative to the anatomical model of the surgical scene; and (i) displaying the direction indicator and the reference view to the user.

15. The method of claim 14, wherein the coordinate space of the cameras is registered to the coordinate space of the patient or the coordinate space of the anatomical model using a calibration matrix, wherein the calibration matrix is determined using a least means square algorithm or a Kalman filter.

16. The method of claim 14, wherein the coordinate space of the cameras is registered to the coordinate space of the patient or the coordinate space of the anatomical model using one or more anatomical landmarks located in or near the surgical scene.

17. The method of claim 14, further comprising using the depth information to generate or update the reference view.

18. A method for imaging a surgical scene of a patient, comprising:
(a) using one or more cameras to capture one or more images of the surgical scene;
(b) using one or more sensors to obtain position information of the one or more cameras;
(c) generating a reference view of the surgical scene based on the position information of the one or more cameras, wherein the reference view includes a field of view of the one or more cameras relative to an anatomical model of the surgical scene;
(d) displaying the reference view and the one or more images of the surgical scene to a user;
(e) using the one or more sensors to obtain orientation information of the one or more cameras;
(f) generating a direction indicator based on the orientation information, wherein the direction indicator corresponds to a direction in which the one or more cameras are oriented relative to the anatomical model of the surgical scene; and
(g) displaying the direction indicator and the reference view to the user, wherein the reference view includes a visual frame indicating a subregion of the reference view relative to the anatomical model of the surgical scene, wherein the subregion corresponds to the field of view of the one or more cameras.

19. The method of claim 18, wherein the frame is resizable to reflect a current field of view of the one or more cameras when (i) a position or an orientation of the one or more cameras changes or (ii) the one or more cameras zoom in or out to adjust the field of view of the one or more cameras.

* * * * *